United States Patent
Feist et al.

(10) Patent No.: US 7,858,952 B2
(45) Date of Patent: Dec. 28, 2010

(54) COATINGS AND A METHOD OF OPTICALLY DETECTING CORROSION IN COATINGS

(75) Inventors: Jörg Feist, London (GB); Andrew Lawrence Heyes, Buckinghamshire (GB)

(73) Assignee: Southside Thermal Sciences (STS) Limited, London (GB)

( * ) Notice: Subject to any disclaimer, the term of this patent is extended or adjusted under 35 U.S.C. 154(b) by 1085 days.

(21) Appl. No.: 10/568,696

(22) PCT Filed: Aug. 18, 2004

(86) PCT No.: PCT/GB2004/003550
§ 371 (c)(1),
(2), (4) Date: Aug. 8, 2006

(87) PCT Pub. No.: WO2005/019601
PCT Pub. Date: Mar. 3, 2005

(65) Prior Publication Data
US 2007/0134518 A1    Jun. 14, 2007

(30) Foreign Application Priority Data
Aug. 18, 2003 (GB) ................... 0319349.7

(51) Int. Cl.
*G01N 21/64* (2006.01)
(52) U.S. Cl. .................................. 250/459.1
(58) Field of Classification Search ........... 250/459.1
See application file for complete search history.

(56) References Cited

U.S. PATENT DOCUMENTS

| | | | |
|---|---|---|---|
| 4,774,150 A * | 9/1988 | Amano et al. | 428/690 |
| 6,190,785 B1 * | 2/2001 | Yonezawa et al. | 428/615 |
| 6,410,926 B1 * | 6/2002 | Munro et al. | 250/459.1 |
| 2003/0068824 A1 * | 4/2003 | Frankel et al. | 436/60 |
| 2003/0115941 A1 * | 6/2003 | Srivastava et al. | 73/118.1 |

FOREIGN PATENT DOCUMENTS
WO     00/06796     10/2000

OTHER PUBLICATIONS

Feist et al., "Oxygen Quenching of Phosphorescence From Thermographic Phosphors", Mar. 2003, Measurement Science and Technology 14 N17-N20, pp. 1-4.
Schulz et al., "The Thermocyclic Behavior of Differently Stabilized and Structured EB-PVD TBCs", Oct. 1997, JOM Research Summary vol. 49, No. 10, pp. 1-10.

* cited by examiner

*Primary Examiner*—David P Porta
*Assistant Examiner*—Marcus H Taningco
(74) *Attorney, Agent, or Firm*—Renner, Otto, Boisselle & Sklar, LLP (57) ABSTRACT

A method for optically detecting hot corrosion of a thermal barrier coating (TBC), comprising: providing a TBC which includes an indicator material which has an optical emission which is altered by corrosion of the coating; irradiating the TBC with an excitation beam of light; receiving an optical emission from the TBC; obtaining a detection signal for the optical emission; and analysing the detection signal to identify one or more predeterminable spectral characteristics and evaluate the amount of corrosion of the TBC. Detection apparatus for optically detecting the corrosion of a thermal barrier coating with the mentioned method, and coating to be inspected by said apparatus and method.

51 Claims, 9 Drawing Sheets

COATINGS AND A METHOD OF OPTICALLY DETECTING CORROSION IN COATINGS

This application is a national phase of International Application No. PCT/GB2004/003550 filed Aug. 18, 2004 and published in English laungage.

The present invention relates to coatings, in particular protective coatings, which are subject to corrosion processes, in particular oxidative corrosion, and a method of optically detecting corrosion in coatings, in particular an extent of corrosion in coatings.

Such coatings include thermal barrier coatings (TBCs), but the present invention extends to any ceramic coatings, in particular oxide-containing ceramic coatings, which are subjected to corrosion.

By way of example, WO-A-00/06796, the content of which is incorporated herein by reference, discloses a TBC which comprises a mixture of at least a ceramic material and an indicator material having an optical emission spectrum which varies in response to a physical parameter.

A typical application for such coatings is in gas turbines, in particular in aviation and power generation, with yttria-stabilized zirconia (YSZ) being the currently preferred coating material.

Ceramic coatings are usually applied to components, typically as formed from metals and metal alloys, which are to be subjected to hostile environments, in particular where the temperature exceeds the melting point of the material of the component or reactions with elements associated with combustion would alter the chemical structure of the material of the component. The ceramic coatings protect the underlying components, such as turbine blades, which can be very expensive, or combustor cans, from early damage and failure.

These protective coatings can be laid down using a variety of deposition techniques and can provide different kinds of protection depending upon the material and the chosen morphology of the coating.

The longevity and effectiveness of these protective coatings during high-temperature operation depends upon many different factors.

In aviation engines, reactions with sand as drawn in by the engine during take-off and landing, and airborne particles, such as volcanic ash, in flight can have a detrimental effect on the coatings. In these examples, owing to the melting point of the substances, damage would be expected to occur at temperatures above 1000° C.

However, when these ceramic coatings are used at high temperatures in combination with fuels, which contain elements such as vanadium, sulfur, sodium, potassium (kalium), etc, chemical reactions can start at temperatures significantly below 1000° C.

As a consequence, the coatings can change their structure and consequently lead to a loss of structural integrity. The levels of these constituents in the fuel can vary widely, depending upon the kind of fuel. As an example, the upper limit for sulfur in aviation fuel is 0.05 wt %, while a typical gas turbine fuel may contain 0.24 wt % sulfur. Higher sulfur content is found in other products. For typical industrial fuels, the sulfur content is 1 wt %, and for some heavy oils is 4 wt %.

As mentioned hereinabove, YSZ is the currently preferred coating material, and although YSZ is apparently more corrosion resistant than other coating materials, such as MCrAlY and aluminide metallic protective coatings, YSZ appears in particular to be susceptible to vanadium hot corrosion. Whilst such corrosion may not be expected to be a problem in aircraft engines when aviation-quality fuel is burnt (>0.05 wt % S; 0 wt % V), low-quality fuel, such as used in power generation applications, can contain appreciable levels of sulfur and particularly vanadium. This appears to pose a particular problem when using coal as an alternative fuel for turbines, for example, in the form of syngas. Although vanadium corrosion could be reduced by the addition of magnesium oxide to the fuel, there is concern as to the formation of particulates, leading to higher erosion and the risk of cooling path blockage.

Hot corrosion of YSZ is mainly driven by the reaction between these pollutants and oxides employed to stabilize the zirconia ($ZrO_2$), that is, yttria ($Y_2O_3$) in YSZ. A possible chemical reaction is given hereinbelow.

$$ZrO_2(Y_2O_3) + V_2O_5 \rightarrow ZrO_2(\text{monoclinic}) + 2YVO_4$$

This chemical mechanism removes the yttria stabilizer, which would cause destabilisation and failure of the YSZ.

It is an aim of the present invention to provide a coating which enables detection of corrosion, and particularly a determination of an extent of such corrosion, and also a method for detecting corrosion in coatings.

The present inventors have determined that the corrosion of coatings can be surprisingly detected with a high degree of sensitivity through the incorporation of a luminescent material, in particular a rare earth dopant, in a coating, where the luminescent material associates, apparently preferentially, with at least one of the reaction products.

To date, luminescent materials have been incorporated in coatings, such as TBCs, to enable characterization of the physical properties of a coating, notably the temperature of the coating where operated in a high-temperature environment, but there has been no recognition whatsoever to the possibility of incorporating a luminescent material in a coating to provide for the optical characterization of a reactant product which arises as a result of a reaction with an environmental corrodant, and in particular enables a determination as to the extent of corrosion by reference to emission spectra for the coating.

In one aspect the present invention provides a method of optically detecting corrosion of a coating, the method comprising the steps of: providing a coating which includes an indicator material which has an optical emission which is altered by corrosion of the coating at the indicator material; irradiating the coating with an excitation beam of light; receiving an optical emission from the coating; obtaining a detection signal for the optical emission; and analyzing the detection signal to identify one or more predeterminable spectral characteristics and characterize corrosion of the coating from the one or more spectral characteristics.

In another aspect the present invention provides a detection apparatus for optically detecting corrosion of a coating which includes an indicator material which has an optical emission which is altered by corrosion of the coating at the indicator material, the apparatus comprising: a light source for irradiating the coating with an excitation beam of light; a detector for receiving an optical emission from the coating and generating a detection signal therefrom; and an analyzer for analyzing the detection signal to identify one or more predeterminable spectral characteristics and characterize corrosion of the coating from the one or more spectral characteristics.

In a further aspect the present invention extends to use of an indicator material in a coating optically to detect corrosion of the coating, wherein the indicator material has an optical emission which is altered by corrosion of the coating at the indicator material.

In a still further aspect the present invention provides a coating including an indicator material for optically detecting corrosion of the coating, wherein the indicator material has an optical emission which is altered by corrosion of the coating at the indicator material.

Figure 1:
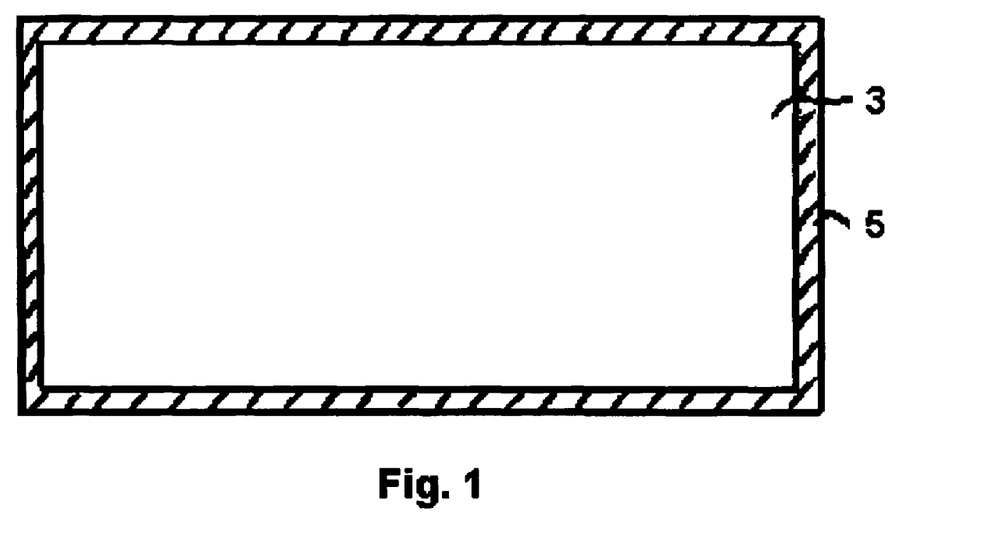
FIG. 1 illustrates a component coated with a coating in accordance with a preferred embodiment of the present invention.

Preferred embodiments of the present invention will now be described hereinbelow by way of example only with reference to the accompanying drawings, in which:

FIG. 1 illustrates a component 3 which is coated with a coating 5 in accordance with a preferred embodiment of the present invention.

The component 3 can be any component which is subjected to a corrosive environment, in particular a high-temperature, corrosive environment, for example, vanadium hot corrosion. Such components include components of a gas turbine engine, for example, a turbine blade, as used in power generation plants.

The coating 5 comprises a ceramic material, in a preferred embodiment a refractory material, which includes an indicator material which associates with at least one reaction product arising as a result of a reaction with an environmental corrodant and has an optical emission which varies in dependence upon the corrosion thereof by the corrodant.

In one embodiment the coating 5 comprises a thermal barrier coating (TBC).

In this embodiment the ceramic material comprises YSZ. In other embodiments the ceramic material could comprise pyrochlore, lanthanum-hexa-aluminate, magnetoplumbite ($LnM_{1+x}Q_xAl_{11-2x}O_{19}$, where $Ln^{3+}$=La->Gd (group of lanthanides from La to Gd), $M^{2+}$=Sr, Mn->Zn (group of elements in the periodic table from Mn to Zn), and $Q^{4+}$=Ti, Si), garnets ($Y_3Al_xFe_{5-x}O_{12}$:YAG) or monazite.

In this embodiment the indicator material comprises a rare earth dopant, and particularly one of europium, dysprosium, terbium and thulium or a mixture thereof.

Figure 2:
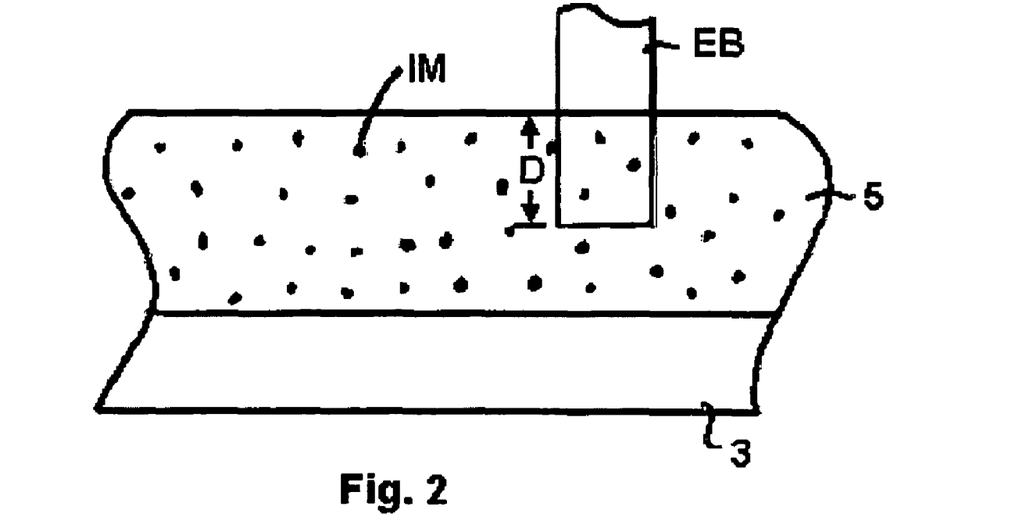
FIG. 2 illustrates a coating in accordance with one embodiment of the present invention.

In one embodiment, as represented schematically in FIG. 2, the coating 5 includes a substantially uniform distribution of an indicator material IM therethroughout. In this embodiment an excitation beam EB irradiates the coating 5 to a predetermined depth D, where the depth D is determined by the wavelength and the intensity of the light of the excitation beam EB. As will be described in more detail hereinbelow, the depth D can be controlled by controlling the wavelength and the intensity of the light of the excitation beam EB, thus providing for a quantitative determination of the extent of corrosion. In one preferred embodiment, through setting the depth D of penetration of the excitation beam EB, a determination can be made as to when the corrosion extends to that depth D. In another preferred embodiment, through one of progressively increasing or decreasing the depth D of penetration of the excitation beam EB, the depth of corrosion can be determined.

Figure 3:
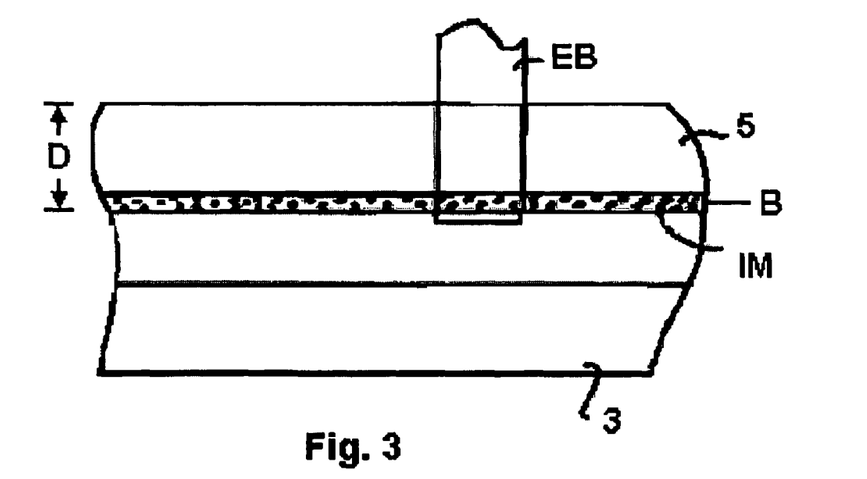
FIG. 3 illustrates a coating in accordance with another embodiment of the present invention.

In another embodiment, as represented schematically in FIG. 3, the coating 5 includes a band B of an indicator material IM at a predetermined depth D from the surface of the coating 5, where the depth D represents an extent beyond which corrosion is unacceptable as the probability that the component 3 is likely to fail exceeds a critical limit. In this embodiment the intensity and wavelength of the excitation beam EB are such that the excitation beam EB extends to the band B of indicator material IM.

Figure 4:
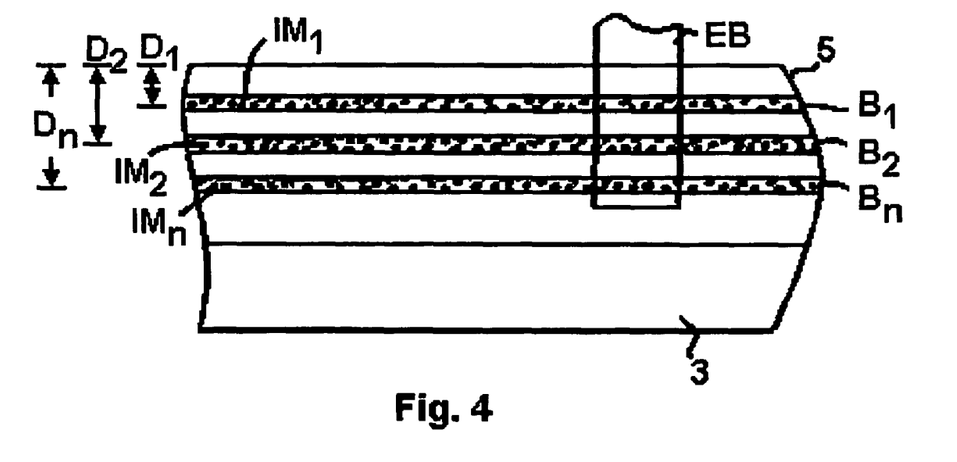
FIG. 4 illustrates a coating in accordance with a further embodiment of the present invention.

In a further embodiment, as represented schematically in FIG. 4, the coating 5 includes a plurality of bands $B_1, B_2 \ldots B_n$ of indicator materials $IM_1, IM_2 \ldots IM_n$ at predetermined depths $D_1, D_2 \ldots D_n$ from the surface of the coating 5, where the predetermined depth $D_n$ of the lowermost band $B_n$, represents an extent beyond which corrosion is unacceptable as the probability that the component 3 is likely to fail exceeds a critical limit.

In one embodiment the bands $B_1, B_2 \ldots B_n$ each include a different indicator material $IM_1, IM_2 \ldots IM_n$. In one embodiment the intensity and wavelength of the excitation beam EB are such as to extend to the lowermost band $B_n$ of indicator material $IM_n$. In another embodiment the excitation beam EB can comprise light of one or more wavelengths and intensities, such that the light of respective ones of the wavelengths extends to respective ones of the bands $B_1, B_2 \ldots B_n$.

In another embodiment at least ones of the bands $B_1, B_2 \ldots B_n$ can include the same indicator material $IM_1, IM_2 \ldots IM_n$. In this embodiment the excitation beam EB comprises light of more than one wavelength, such that the light of respective ones of the wavelengths extends to respective ones of the bands $B_1, B_2 \ldots B_n$.

The coating 5 is applied using a known deposition technique, such as chemical vapor deposition (CVD), electron beam physical vapor deposition (EBPVD), plasma spray deposition (PSD), electrostatic-assisted vapor deposition (ESAVD), sol-gel deposition and sputtering deposition. In one embodiment an initial bondcoat/interlayer may be deposited prior to the coating 5 to improve the performance of the coating 5.

Figure 5:
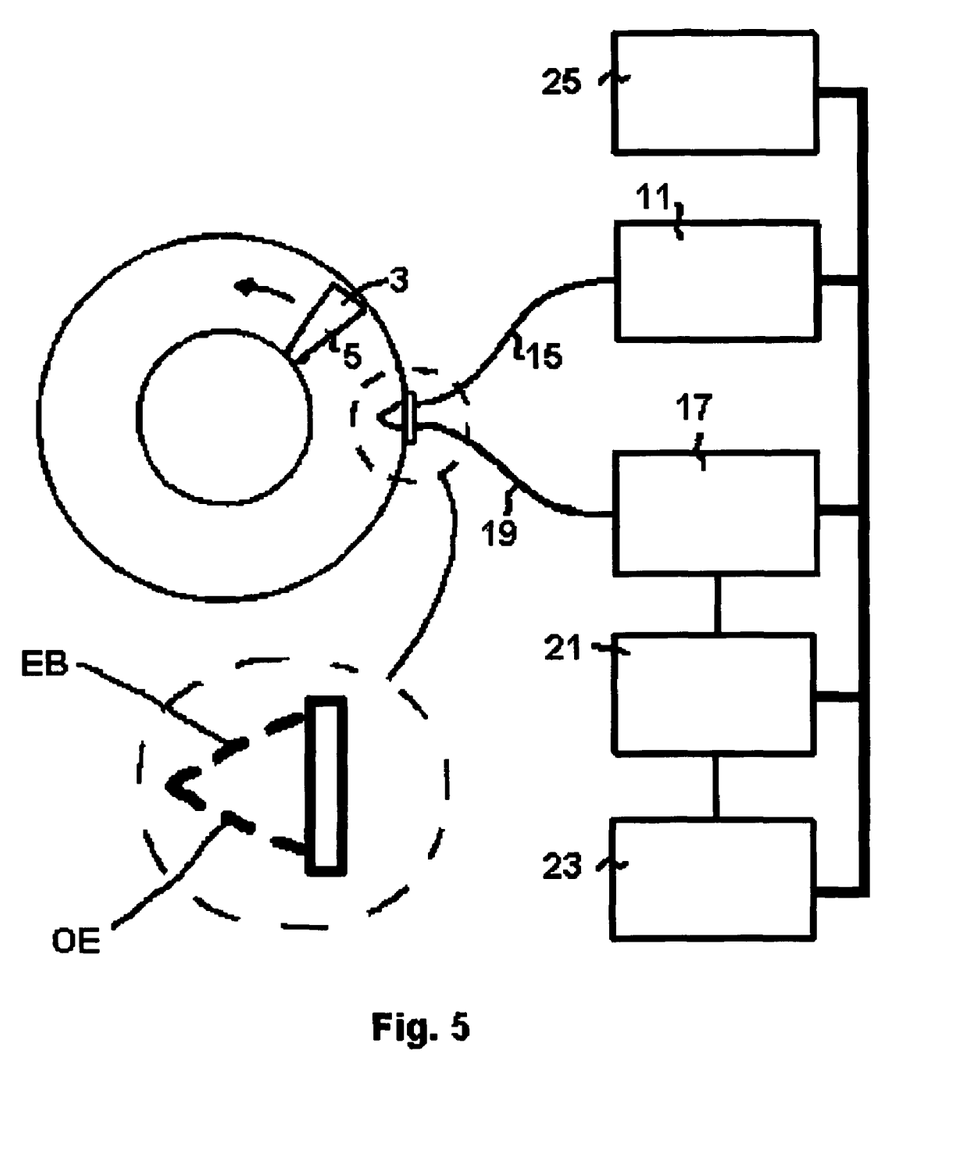
FIG. 5 schematically illustrates a detection apparatus in accordance with a preferred embodiment of the present invention.

FIG. 5 illustrates a detection apparatus for detecting the state of the coating 5 of a component 3 in accordance with a preferred embodiment of the present invention.

In this embodiment, and by way of exemplification only, the component 3 forms part of a machine and particularly a moving part, here a turbine blade of a gas turbine engine, but could equally be a static part of a machine.

The detection apparatus comprises a light source 11, in this embodiment a laser, here a Nd:YAG pulsed laser, for generating an interrogating excitation beam EB for interrogating the coating 5 of a component 3, and a first waveguide 15, here an optical fiber, which is optically coupled to the light source 11 to direct the interrogating excitation beam EB onto the component 3. In this embodiment, where the component 3 is a moving part, the component 3 is irradiated by the excitation beam EB on each pass of the component 3. In preferred embodiments the light source 11 is configured to deliver light at wavelengths one or both of 266 nm and 532 nm.

In alternative embodiments the light source 11 could comprise a light-emitting emitting diode, a light-emitting laser diode, a mercury lamp or a xenon lamp.

The detection apparatus further comprises a detector 17 for receiving an optical emission OE from the coating 5 on the component 3 and generating a detection signal, and a second waveguide 19, here an optical fiber, which is optically coupled to the detector 17 to direct the optical emission OE from the coating 5 of the component 3 to the detector 17. In this embodiment, where the component 3 is a moving part, the optical emission OE is received from the coating 5 of the component 3 on each pass of the component 3.

In one embodiment the first and second waveguides 15, 19 comprise separate optical elements. In an alternative embodiment, through the use of a directional coupler, the first and second waveguides 15, 19 could be provided by a single optical element.

In another embodiment the waveguides 15, 19 could be omitted, with the excitation beam EB and the optical-emission OE having an open path. The detection apparatus further comprises an analyzer 21 which is operably connected to the detector 17 to receive the detection signal therefrom and analyze the detection signal such as to identify one or more predetermined spectral characteristics and characterize the state of the coating 5 of the component 3 from the one or more spectral characteristics, as will be described in more detail hereinbelow.

The detection apparatus further comprises an output device 23 which is operably connected to the analyzer 21 and provides information to an operator concerning the state of the coating 5 of the component 3. In a preferred embodiment the output device 23 includes a display for visually displaying information concerning the state of the coating 5 of the component 3, but can also include an audio output so as audibly to warn an operator concerning the state of the coating 5 of the component 3. In one embodiment, as in this embodiment, where the component 3 is part of a machine, the output device 23 can be configured to control operation of the machine, such as to provide for the machine to be shut down in the event of the state of the coating 5 of the component 3 being determined to be below a threshold state.

The detection apparatus further comprises a controller 25 which is operably connected to the light source 11, the detector 17, the analyzer 21 and the output device 23 to control the operation of the same. In one embodiment, as will be described in more detail hereinbelow, the controller 25 is operative to control the light source 11, and in particular the intensity and the wavelength of the light of the excitation beam EB, such as to control the depth of penetration of the excitation beam EB into the coating 5, thus enabling a determination as to the extent of the depth of corrosion into the coating 5.

Operation of the detection apparatus will now be described hereinbelow in relation to various modes of operation.

In one embodiment, where the coating 5 includes a substantially uniform distribution of an indicator material IM, as illustrated in FIG. 2, the analyzer 21 characterizes the corrosion of the coating 5 by reference to one or more signal peaks corresponding to material of the coating 5 where not corroded and a reaction product resulting from the reaction of the material of the coating 5 and an environmental corrodant, with the intensity of the one or more signal peaks being utilized to determine the extent of the corrosion.

Figure 6A:
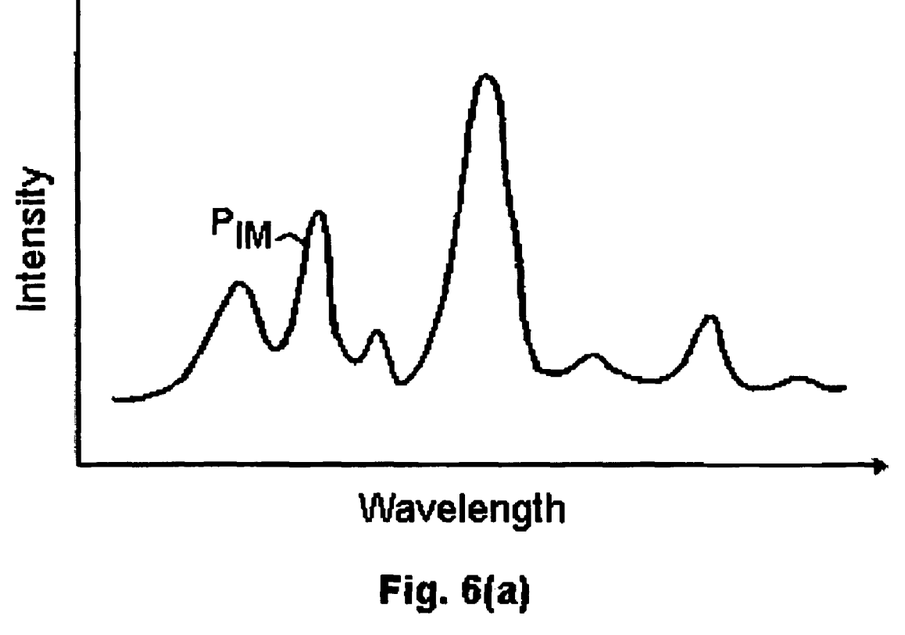
FIGS. 6(a) to (c) illustrate emission spectra for a coating in accordance with one embodiment of the present invention where subjected to corrosion by a corrodant.

FIG. 6(a) represents the detection signal for a coating 5 which has not been subjected to any corrosion, in which detection signal is present at least one signal peak PIM corresponding to at least one material of the coating 5.

Figure 6B:
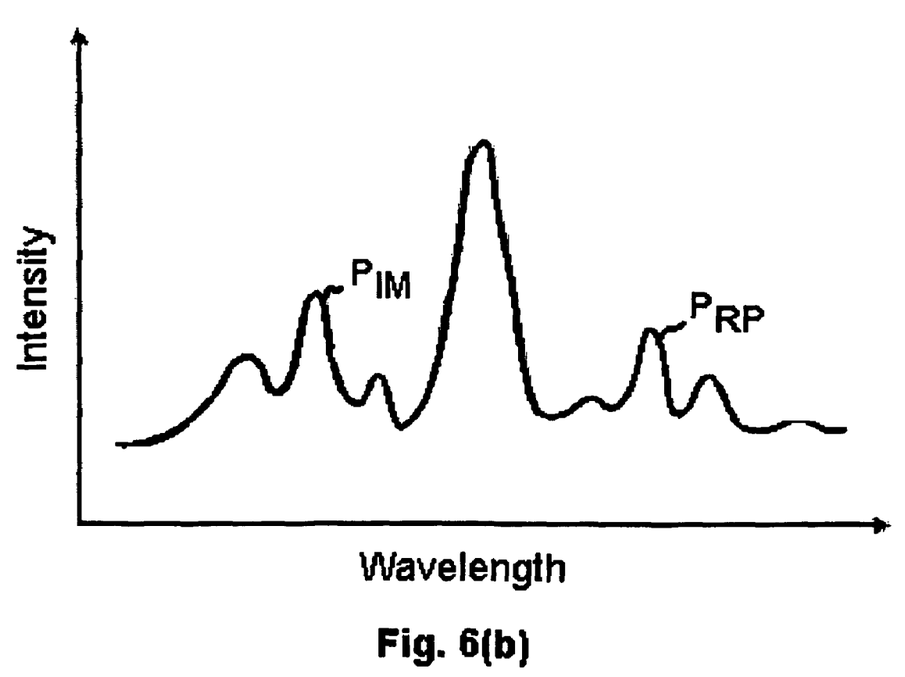

FIG. 6(b) represents the detection signal for the coating 5 where subjected to a corrosive environment for a first period of time, in which detection signal is present the at least one signal peak $P_{IM}$ corresponding to the at least one material of the coating 5, but at a reduced intensity as compared to the detection signal absent any corrosion, and at least one signal peak $P_{RP}$ corresponding to a reaction product of the at least one material of the coating 5 and the corrodant.

Figure 6C:
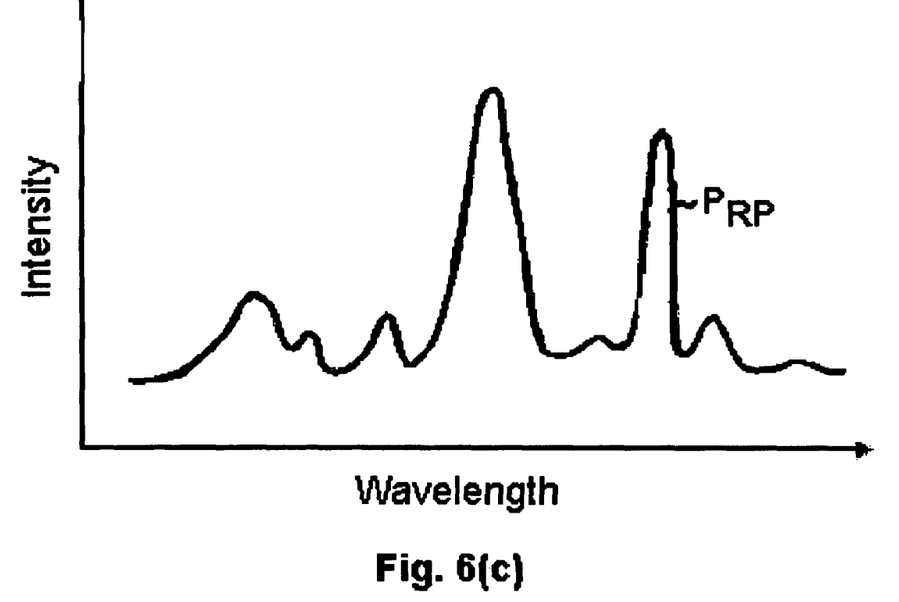

FIG. 6(c) represents the detection signal for the coating 5 where subjected to the corrosive environment for a second, extended period of time, in which detection signal is present the at least one signal peak $P_{RP}$ corresponding to the reaction product, but at an increased intensity as compared to the detection signal for the first period of time, and the at least one signal peak $P_{IM}$ corresponding to the at least one material of the coating 5 is absent.

In one embodiment by periodically analyzing the intensities of the signal peaks $P_{IM}$, $P_{RP}$ corresponding to the at least one material of the coating 5 and the reaction product, and in a preferred embodiment the relative intensities thereof, typically by way of an intensity ratio, the analyzer 21 determines the depth of the corrosion, in this embodiment with reference to a calibrated standard. Where, as in the detection signal of FIG. 6(c), a point in time is reached where the detection signal does not include a signal peak $P_{IM}$ corresponding to the at least one material of the coating 5, the corrosion is determined to have progressed to the predetermined depth, which corresponds to the depth D of penetration of the irradiating excitation beam EB.

In another embodiment by one of progressively increasing or decreasing the depth D of penetration of the excitation beam EB and analyzing the intensity of at least one of the signal peaks $P_{IM}$, $P_{RP}$ corresponding to the at least one material of the coating 5 and the reaction product, and in a preferred embodiment the relative intensities thereof, typically by way of an intensity ratio, the analyzer 21 determines the depth of the corrosion.

Reference is now made to the following non-limiting Example which exemplifies the present invention in relation to the corrosion of YSZ, where including a europium dopant as an indicator material, by reaction with vanadium pentoxide ($V_2O_5$).

EXAMPLE

8YSZ having 3 mol % of yttria doped with europium $((Y_{0.97}Eu_{0.03})O_{1.5})_{0.08}$—$(ZrO_2)_{0.92}$) was mixed with $V_2O_5$ in a weight ratio of 16:1, and heated in a platinum crucible at 700° C. for 2 hours. This reaction of YSZ with $V_2O_5$ is intended to simulate vanadium hot corrosion of a turbine coating.

Figure 7:
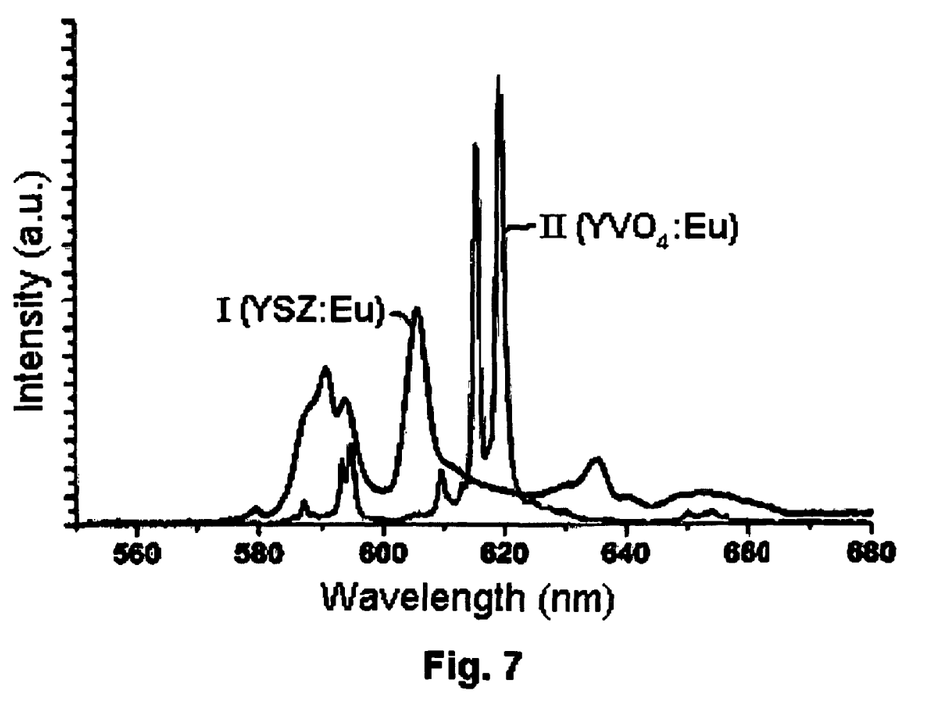
FIG. 7 illustrates emission spectra for (I) a YSZ:Eu material prior to a corrosion reaction and (II) the resulting $YVO_4$:Eu product following reaction with $V_2O_5$.

Luminescence spectra, as obtained by excitation with a laser pulse having a wavelength of 266 nm, were obtained for the YSZ:Eu material prior to the corrosion reaction and for the resulting products following reaction. FIG. 7 illustrates these luminescence spectra, with trace I being that of the YSZ:Eu material prior to the corrosion reaction, and trace II being that of the resulting europium-doped yttrium vanadate ($YVO_4$:Eu) product following the corrosion reaction. As can be clearly observed, the emission spectrum (trace II) is altered markedly by the reaction with $V_2O_5$. The emission spectrum (trace I) for the YSZ:Eu material prior to the corrosion reaction includes an intense signal peak at 606 nm, and the emission spectrum (trace II) following the corrosion reaction includes two intense signal peaks between 610 and 625 nm, where the signal peak at 620 nm corresponds to $YVO_4$:Eu.

Reference to these signal peaks thus provides a clear measure as to the vanadium hot corrosion of YSZ:Eu material.

Figure 8:
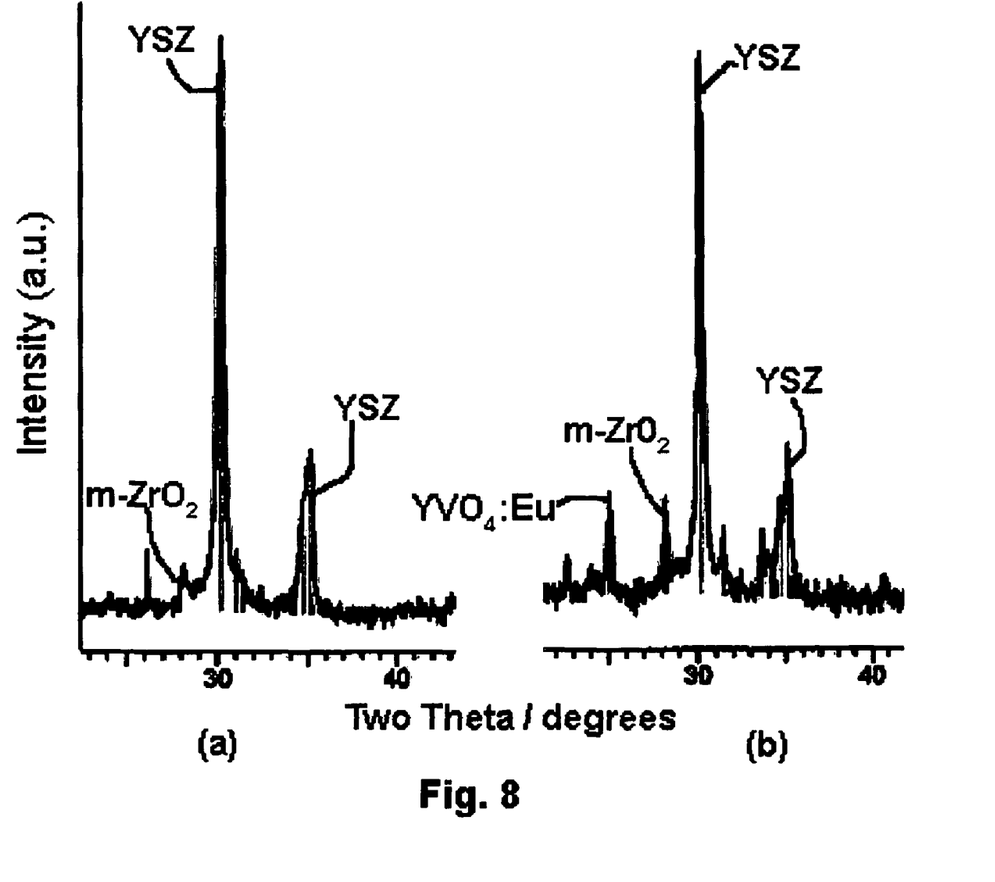
FIG. 8 illustrates X-ray diffraction (XRD) spectra for a mixture of a YSZ:Eu material and $V_2O_5$ prior to a corrosion reaction and the resulting products following reaction.

XRD spectra were also obtained for a mixture of the YSZ:Eu material and $V_2O_5$ prior to the corrosion reaction and the resulting products following the corrosion reaction. FIGS. 8(a) and (b) illustrate these XRD spectra, with FIG. 8(a) being that of a region of the XRD spectrum for the mixture of the YSZ:Eu material and $V_2O_5$ prior to the corrosion reaction, and FIG. 8(b) being that of a region of the XRD spectrum for the resulting products following the corrosion reaction. As can be clearly observed, the reaction products include $YVO_4$:Eu and a significantly higher fraction of monoclinic (m) $ZrO_2$.

In another embodiment, where the coating 5 includes a single band B of an indicator material IM, as illustrated in FIG. 3, the analyzer 21 characterizes the corrosion of the coating 5 by the presence of one or more signal peaks corresponding to a reaction product of at least one material of the coating 5 from within the band B and an environmental corrodant.

Figure 9A:
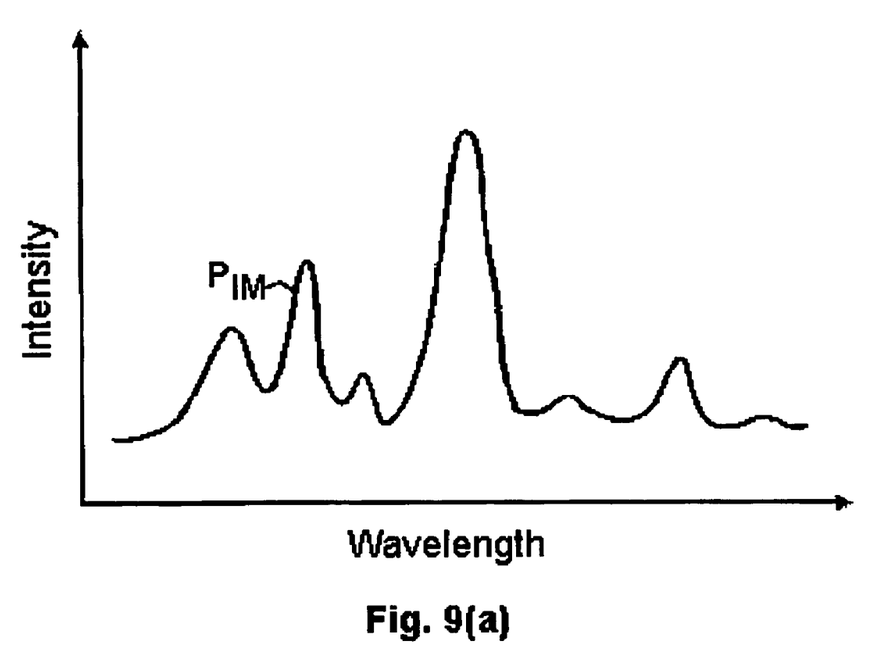
FIGS. 9(a) and (b) illustrate emission spectra for a coating in accordance with another embodiment of the present invention where subjected to corrosion by a corrodant.

FIG. 9(a) represents the detection signal for a coating 5 where subjected to a corrosive environment but the corrosion has not reached band B of indicator material IM, in which detection signal is present at least one signal peak $P_{IM}$ corresponding to the at least one material of the coating 5 from within the band B.

Figure 9B:
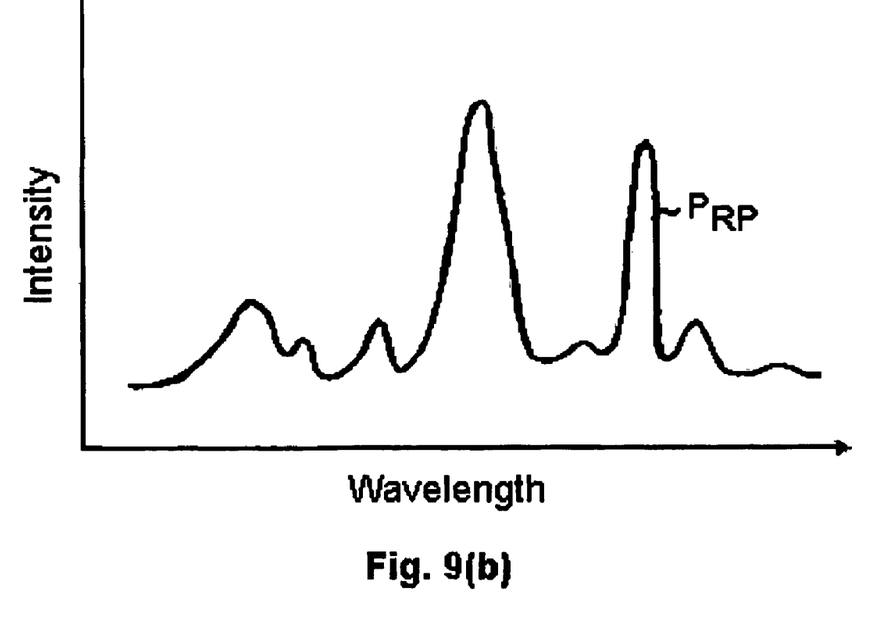

FIG. 9(b) represents the detection signal for the coating 5 where subjected to a corrosive environment for an extended period of time and the corrosion extends to the band B of indicator material IM, in which detection signal is present the at least one signal peak $P_{RP}$ corresponding to a reaction product of the at least one material of the coating 5 from within the band B and the corrodant, and the at least one signal peak $P_{IM}$ corresponding to the at least one material of the coating 5 from within the band B is absent.

By periodically analyzing the detection signals for the signal peaks $P_{IM}$, $P_{RP}$ corresponding to the at least one material of the coating 5 from within the band B and the reaction product, the analyzer 21 determines that the corrosion extends to the depth D of the band B of indicator material IM by the presence of at least one signal peak $P_{RP}$ corresponding to the reaction product, and in a preferred embodiment the absence of a signal peak $P_{IM}$ corresponding to the at least one material of the coating 5 from within the band B.

In a further embodiment, where the coating 5 includes a plurality of bands $B_1$, $B_2$ ... $B_n$ of indicator material $IM_1$, $IM_2$ ... $IM_n$, as illustrated in FIG. 4, the analyzer 21 characterizes the corrosion of the coating 5 by the presence of one or more signal peaks $P_{RP1}$, $P_{RP1}$ ... $P_{RPn}$ corresponding to reaction products resulting from the reaction of at least one material of the coating 5 from within the bands $B_1$, $B_2$ ... $B_n$ and an environmental corrodant.

In one preferred embodiment the indicator materials $IM_1$, $IM_2$ ... $IM_n$ in each of the bands $B_1$, $B_2$ ... $B_n$ is different, such that the optical emission OE includes signal peaks corresponding to each of the indicator materials $IM_1$, $IM_2$ ... $IM_n$.

In another preferred embodiment the indicator materials $IM_1$, $IM_2$ ... $IM_n$ of at least ones of the bands $B_1$, $B_2$ ... $B_n$ are the same and the irradiating excitation beam EB includes light of different wavelength, such that the optical emission OE includes signal peaks corresponding to each of the indicator materials $IM_1$, $IM_2$ ... $IM_n$. In an alternative embodiment the light source 11 could be configured to deliver a plurality of excitation beams EB of light of different wavelength.

Where the extent of the corrosion has not reached any of the bands $B_1$, $B_2$ ... $B_n$ of indicator materials $IM_1$, $IM_2$ ... $IM_n$, the detection signal includes signal peaks $P_{IM1}$, $P_{IM1}$ ... $P_{IMn}$ corresponding to at least one material of the coating 5 from within each of the bands $B_1$, $B_2$ ... $B_n$, but, as the corrosion extends progressively through respective ones of the bands $B_1$, $B_2$ ... $B_n$, the detection signal includes signal peaks $P_{RP1}$, $P_{RP1}$ ... $P_{RPn}$ corresponding to reaction products of respective ones of the at least one material of the coating 5 from within the respective bands $B_1$, $B_2$ ... $B_n$ and the corrodant.

Figure 10A:
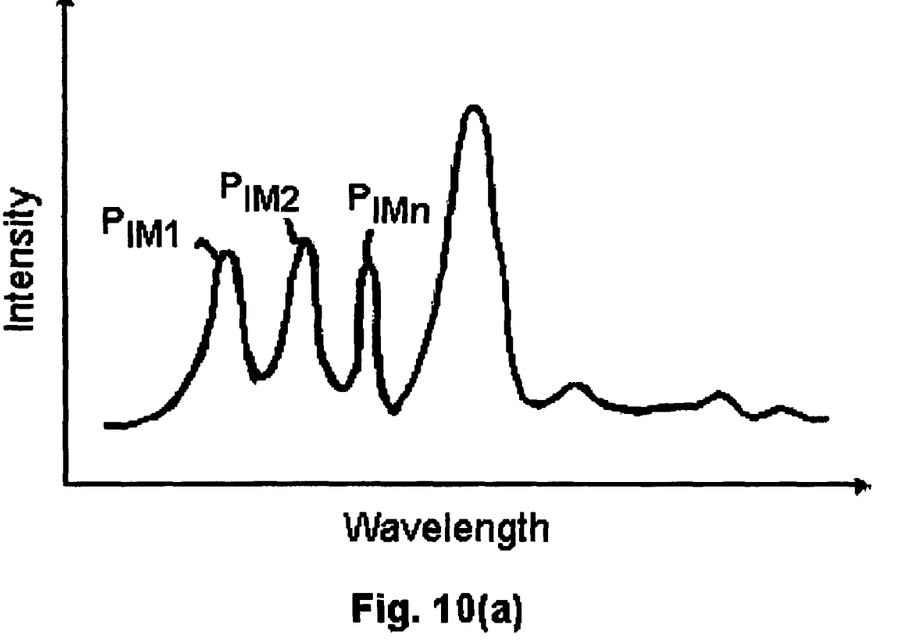
FIGS. 10(a) to (d) illustrate emission spectra for a coating in accordance with a further embodiment of the present invention where subjected to corrosion by a corrodant.

FIG. 10(a) represents the detection signal for a coating 5 where subjected to a corrosive environment but the corrosion has not reached the first, uppermost band $B_1$ of indicator material $IM_1$, in which detection signal is present signal peaks $P_{IM1}$, $P_{IM2}$ ... $P_{IMn}$ corresponding to at least one material of the coating 5 from within each of the bands $B_1$, $B_2$ ... $B_n$.

Figure 10B:
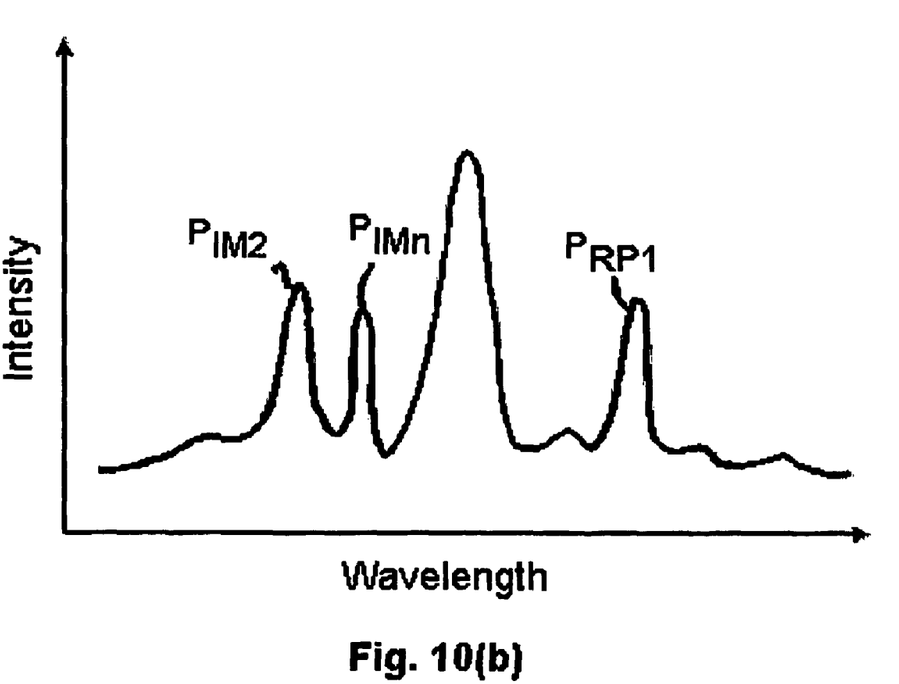

FIG. 10(b) represents the detection signal for the coating 5 where subjected to a corrosive environment for a further period of time and the corrosion extends to the first band $B_1$ of indicator material $IM_1$, in which detection signal is present the at least one signal peak $P_{RP1}$ corresponding to a reaction product of at least one material of the coating 5 from within the first band $B_1$ of indicator material $IM_1$ and the corrodant, and signal peaks $P_{IM2}$ ... $P_{IMn}$ corresponding to at least one material of the coating 5 from within each of the other bands $B_2$ ... $B_n$.

Figure 10C:
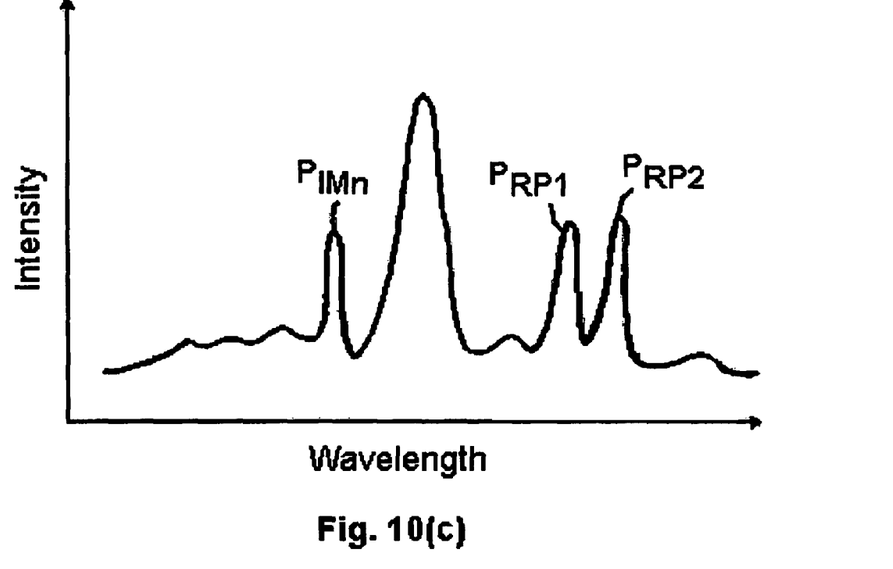

FIG. 10(c) represents the detection signal for the coating 5 where subjected to a corrosive environment for a yet further period of time and the corrosion extends to the second band $B_2$ of indicator material $IM_2$, in which detection signal is present signal peaks $P_{RP1}$, $P_{RP2}$ corresponding to reaction products of at least one material of the coating 5 from within the first and second bands $B_1$, $B_2$ of indicator material $IM_1$, $IM_2$ and the corrodant, and at least one signal peak $P_{IMn}$ corresponding to at least one material of the coating 5 from within the other band $B_n$.

Figure 10D:
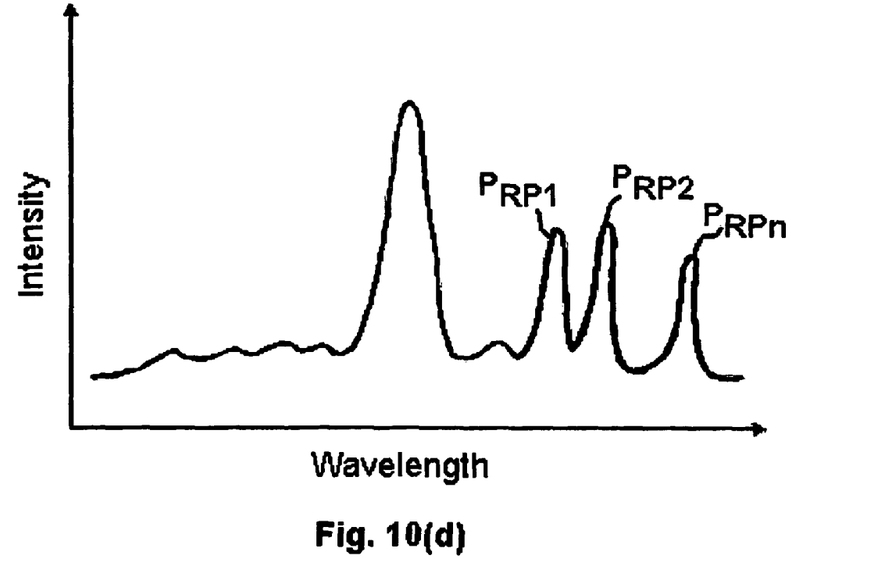

FIG. 10(d) represents the detection signal for the coating 5 where subjected to a corrosive environment for a still further period of time and the corrosion extends to the lowermost band $B_n$ of indicator material $IM_n$, in which detection signal is present signal peaks $P_{RP1}$, $P_{RP1}$ ... $P_{RPn}$ corresponding to reaction products of at least one material of the coating 5 from within each of the bands $B_1$, $B_2$ ... $B_n$ of indicator materials $IM_1$, $IM_2$ ... $IM_n$ and the corrodant.

By analyzing the detection signals for signal peaks $P_{IM1}$, $P_{IM1}$ ... $P_{IMn}$, $P_{RP1}$, $P_{RP1}$ ... $P_{RPn}$ corresponding to the at least one material of the coating 5 from within the bands $B_1$, $B_2$ ... $B_n$ of indicator materials $IM_1$, $IM_2$ ... $IM_n$ and reaction products of the at least one material of the coating 5 from within the bands $B_1$, $B_2$ ... $B_n$ of indicator materials $IM_1$, $IM_2$ ... $IM_n$ and the corrodant, the analyzer 21 determines that the corrosion extends to a respective one of the depths $D_1$, $D_2$ ... $D_n$ of the bands $B_1$, $B_2$ ... $B_n$ of indicator materials $IM_1$, $IM_2$ ... $IM_n$ by the presence of at least one signal peak $P_{RP1}$, $P_{RP1}$ ... $P_{RPn}$ corresponding to reaction products of at least one material of the coating 5 from within the bands $B_1$, $B_2$ ... $B_n$ of indicator materials $IM_1$, $IM_2$ ... $IM_n$ and the corrodant, and in a preferred embodiment the absence of a signal peak $P_{IM1}$, $P_{IM2}$ ... $P_{IMn}$ corresponding to the at least one material of the coating 5 from within the respective bands $B_1$, $B_2$ ... $B_n$ of indicator materials $IM_1$, $IM_2$ ... $IM_n$.

Finally, it will be understood that the present invention has been described in its preferred embodiments and can be modified in many different ways without departing from the scope of the invention as defined by the appended claims.

The invention claimed is:

1. A method of optically detecting corrosion of a coating, the method comprising the steps of:
providing a coating which includes an indicator material which has an optical emission which is altered by corrosion of the coating at the indicator material;
irradiating the coating with an excitation beam of light;
receiving an optical emission from the coating;
obtaining a detection signal for the optical emission; and
analyzing the detection signal to identify a presence of at least one signal peak corresponding to at least one reaction product of at least one material of the coating and a corrodant, and characterize corrosion of the coating by reference to the at least one signal peak.

2. The method of claim 1, wherein the coating includes a distribution of indicator material therethroughout.

3. The method of claim 2, wherein the excitation beam has a predeterminable intensity and wavelength, such as to irradiate the coating to a predeterminable depth.

4. The method of claim 1, wherein an extent of corrosion is determined by reference to an intensity of the at least one signal peak.

5. The method of claim 4, wherein the extent of corrosion is determined by further reference to a calibration standard.

6. The method of claim 1, wherein the coating includes a band of indicator material at a predeterminable depth therewithin.

7. The method of claim 1, wherein the coating includes a plurality of bands at predeterminable depths therewithin.

8. The method of claim 7, wherein each of the bands includes a different indicator material.

9. The method of claim 7, wherein at least ones of the bands include the same indicator material.

10. The method of claim 1, wherein the coating comprises a ceramic material.

11. The method of claim 10, wherein the coating comprises an oxide-containing ceramic.

12. The method of claim 11, wherein the coating comprises yttria-stabilized zirconia (YSZ), pyrochlore, lanthanum-hexa-aluminate, magnetoplumbite ($LnM_{1+x}Q_xAl_{11-2x}O_{19}$, where $Ln^{3+}$=La-→Gd (group of lanthanides from La to Gd), $M^{2+}$=Sr, Mn-→Zn (group of elements in the periodic table from Mn to Zn), and $Q^{4+}$=Ti, Si), garnets ($Y_3Al_xFe_{5-x}O_{12}$: YAG) or monazite.

13. The method of claim 1, wherein the coating is a thermal barrier coating.

14. The method of claim 1, wherein the indicator material comprises a rare earth dopant.

15. The method of claim 14, wherein the indicator material comprises at least one of europium, dysprosium, terbium and thulium.

16. A method of optically detecting corrosion of a coating, the method comprising the steps of:
providing a coating which includes an indicator material which has an optical emission which is altered by corrosion of the coating at the indicator material;
irradiating the coating with an excitation beam of light;
receiving an optical emission from the coating;
obtaining a detection signal for the optical emission; and
analyzing the detection signal to identify a presence of at least one signal peak corresponding to at least one material of the coating where not corroded, and characterizing corrosion of the coating by reference to the at least one signal peak.

17. The method of claim 16, wherein an extent of corrosion is determined by reference to an intensity of the at least one signal peak.

18. The method of claim 17, wherein the extent of corrosion is determined by further reference to a calibration standard.

19. The method of claim 16, wherein the coating includes a distribution of indicator material therethroughout.

20. The method of claim 19, wherein the excitation beam has a predeterminable intensity and wavelength, such as to irradiate the coating to a predeterminable depth.

21. The method of claim 16, wherein the coating includes a band of indicator material at a predeterminable depth therewithin.

22. The method of claim 16, wherein the coating includes a plurality of bands at predeterminable depths therewithin.

23. The method of claim 22, wherein each of the bands includes a different indicator material.

24. The method of claim 22, wherein at least ones of the bands include the same indicator material.

25. The method of claim 16, wherein the coating comprises a ceramic material.

26. The method of claim 16, wherein the coating comprises an oxide-containing ceramic.

27. The method of claim 16, wherein the coating comprises yttria-stabilized zirconia (YSZ), pyrochlore, lanthanum-hexa-aluminate, magnetoplumbite ($LnM_{1+x}Q_xAl_{11-2x}O_{19}$, where $Ln^{3+}$=La-→Gd (group of lanthanides from La to Gd), $M^{2+}$=Sr, Mn-→Zn (group of elements in the periodic table from Mn to Zn), and $Q^{4+}$=Ti, Si), garnets ($Y_3Al_xFe_{5-x}O_{12}$: YAG) or monazite.

28. The method of claim 16, wherein the coating is a thermal barrier coating.

29. The method of claim 16, wherein the indicator material comprises a rare earth dopant.

30. The method of claim 16, wherein the indicator material comprises at least one of europium, dysprosium, terbium and thulium.

31. A method of optically detecting corrosion of a coating, the method comprising the steps of:
providing a coating which includes an indicator material which has an optical emission which is altered by corrosion of the coating at the indicator material;
irradiating the coating with an excitation beam of light;
receiving an optical emission from the coating;
obtaining a detection signal for the optical emission; and
analyzing the detection signal to identify a presence of at least one signal peak corresponding to at least one material of the coating where not corroded and at least one signal peak corresponding to at least one reaction product of the at least one material of the coating and a corrodant, and characterizing corrosion of the coating by reference to the identified signal peaks.

32. The method of claim 31, wherein an extent of corrosion is determined by reference to relative intensities of the identified signal peaks.

33. The method of claim 32, wherein the extent of corrosion is determined by further reference to a calibration standard.

34. The method of claim 31, wherein the coating includes a distribution of indicator material therethroughout.

35. The method of claim 34, wherein the excitation beam has a predeterminable intensity and wavelength, such as to irradiate the coating to a predeterminable depth.

36. The method of claim 31, wherein the coating includes a band of indicator material at a predeterminable depth therewithin.

37. The method of claim 31, wherein the coating includes a plurality of bands at predeterminable depths therewithin.

38. The method of claim 37, wherein each of the bands includes a different indicator material.

39. The method of claim 37, wherein at least ones of the bands include the same indicator material.

40. The method of claim 31, wherein the coating comprises a ceramic material.

41. The method of claim 31, wherein the coating comprises an oxide-containing ceramic.

42. The method of claim 31, wherein the coating comprises yttria-stabilized zirconia (YSZ), pyrochlore, lanthanum-hexa-aluminate, magnetoplumbite ($LnM_{1+x}Q_xAl_{11-2x}O_{19}$, where $Ln^{3+}$=La-→Gd (group of lanthanides from La to Gd), $M^{2+}$=Sr, Mn-→Zn (group of elements in the periodic table from Mn to Zn), and $Q^{4+}$=Ti, Si), garnets ($Y_3Al_xFe_{5-x}O_{12}$: YAG) or monazite.

43. The method of claim 31, wherein the coating is a thermal barrier coating.

44. The method of claim 31, wherein the indicator material comprises a rare earth dopant.

45. The method of claim 31, wherein the indicator material comprises at least one of europium, dysprosium, terbium and thulium.

46. A method of optically detecting corrosion of a coating, the method comprising the steps of:
providing a coating which includes a band of indicator material which has an optical emission which is altered by corrosion of the coating at the indicator material;
irradiating the coating with an excitation beam of light;
receiving an optical emission from the coating;
obtaining a detection signal for the optical emission; and
analyzing the detection signal to identify a presence of at least one signal peak corresponding to at least one reaction product of at least one material of the coating from within the band of indicator material and a corrodant, and characterizing corrosion of the coating by reference to the at least one signal peak.

47. A method of optically detecting corrosion of a coating, the method comprising the steps of:
providing a coating which includes a band of indicator material which has an optical emission which is altered by corrosion of the coating at the indicator material;
irradiating the coating with an excitation beam of light;
receiving an optical emission from the coating;
obtaining a detection signal for the optical emission; and
analyzing the detection signal to identify a presence of at least one signal peak corresponding to at least one material of the coating where not corroded from within the band of indicator material, and characterizing corrosion of the coating by reference to the at least one signal peak.

48. A method of optically detecting corrosion of a coating, the method comprising the steps of:
providing a coating which includes a plurality of bands of indicator material which has an optical emission which is altered by corrosion of the coating at the indicator material, wherein the plurality of bands are at predeterminable depths within the coating;
irradiating the coating with an excitation beam of light;
receiving an optical emission from the coating;
obtaining a detection signal for the optical emission; and
analyzing the detection signal to identify a presence of at least one signal peak corresponding to at least one reaction product of at least one material of the coating from within the bands of indicator material and a corrodant, and characterizing corrosion of the coating by reference to the at least one signal peak.

49. The method of claim 48, wherein an extent of corrosion is determined by determining a lowermost band from which at least one signal peak corresponding to the at least one reaction product is present.

50. A method of optically detecting corrosion of a coating, the method comprising the steps of:
providing a coating which includes a plurality of bands of indicator material which has an optical emission which is altered by corrosion of the coating at the indicator material, wherein the plurality of bands are at predeterminable depths within the coating;
irradiating the coating with an excitation beam of light;
receiving an optical emission from the coating;
obtaining a detection signal for the optical emission; and
analyzing the detection signal to identify a presence of at least one signal peak corresponding to at least one material of the coating where not corroded from within the bands of indicator material, and characterizing corrosion of the coating by reference to the at least one signal peak.

51. The method of claim 50, wherein an extent of corrosion is determined by determining a lowermost band from which at least one signal peak corresponding to the at least one material of the coating is absent.

* * * * *